United States Patent
Peppel

(10) Patent No.: US 7,314,061 B2
(45) Date of Patent: Jan. 1, 2008

(54) NEEDLELESS ACCESS PORT VALVES

(75) Inventor: Peter W. Peppel, Nazareth, PA (US)

(73) Assignee: B. Braun Medical Inc., Bethlehem, PA (US)

( * ) Notice: Subject to any disclaimer, the term of this patent is extended or adjusted under 35 U.S.C. 154(b) by 292 days.

(21) Appl. No.: 11/090,721

(22) Filed: Mar. 25, 2005

(65) Prior Publication Data

US 2006/0213563 A1    Sep. 28, 2006

(51) Int. Cl.
*F16K 27/02* (2006.01)
(52) U.S. Cl. .................. 137/605; 251/149; 251/149.1; 604/246
(58) Field of Classification Search ............... 251/149, 251/149.1, 149.3, 342; 137/454.2, 605; 604/246
See application file for complete search history.

(56) References Cited

U.S. PATENT DOCUMENTS

| | | | |
|---|---|---|---|
| 2,964,292 A * | 12/1960 | Noir ........................... 251/342 |
| 4,197,848 A | 4/1980 | Garrett et al. |
| 4,456,223 A * | 6/1984 | Ebling ....................... 251/342 |
| 4,535,819 A | 8/1985 | Atkinson et al. |
| 4,745,950 A * | 5/1988 | Mathieu .................... 137/798 |
| 4,765,588 A | 8/1988 | Atkinson |
| 4,934,655 A | 6/1990 | Blenkush et al. |
| 4,953,594 A | 9/1990 | Von Berg |
| 4,955,407 A * | 9/1990 | Inoue ...................... 137/454.2 |
| 5,006,114 A | 4/1991 | Rogers et al. |
| 5,049,128 A | 9/1991 | Duquette |
| 5,061,253 A * | 10/1991 | Yoshida ..................... 604/246 |
| 5,065,783 A | 11/1991 | Ogle, II |
| 5,104,389 A | 4/1992 | Deem et al. |
| 5,108,380 A | 4/1992 | Herlitze et al. |
| 5,147,333 A | 9/1992 | Raines |
| 5,163,922 A | 11/1992 | McElveen, Jr. et al. |
| 5,203,775 A | 4/1993 | Frank et al. |
| 5,230,706 A | 7/1993 | Duquette |
| 5,242,393 A | 9/1993 | Brimhall et al. |
| 5,242,423 A | 9/1993 | Goodsir et al. |
| 5,251,873 A | 10/1993 | Atkinson et al. |
| 5,269,771 A | 12/1993 | Thomas et al. |
| 5,281,206 A | 1/1994 | Lopez |
| 5,289,849 A | 3/1994 | Paradis |
| 5,330,450 A | 7/1994 | Lopez |
| 5,344,414 A | 9/1994 | Lopez et al. |
| 5,353,837 A | 10/1994 | Faust |
| 5,360,413 A | 11/1994 | Leason et al. |
| 5,380,306 A | 1/1995 | Brinon |
| 5,390,898 A | 2/1995 | Smedley et al. |
| 5,395,348 A | 3/1995 | Ryan |
| 5,401,245 A | 3/1995 | Haining |
| 5,423,791 A | 6/1995 | Bartlett |
| 5,425,465 A | 6/1995 | Healy |

(Continued)

*Primary Examiner*—Stephen M. Hepperle
(74) *Attorney, Agent, or Firm*—Christie Parker & Hale LLP

(57) ABSTRACT

Needleless access port valves are generally discussed herein with particular discussions extended to needleless access port valves comprising a stretched body. In one aspect of the present invention, a plug is positioned inside a slip port. When the plug is pushed by a medical implement and moves to a second position, the plug abuts the valve body and stretches the valve body. When the medical implement is subsequently removed, the stretched body forces the plug back to its first position.

19 Claims, 2 Drawing Sheets

U.S. PATENT DOCUMENTS

| | | |
|---|---|---|
| 5,439,451 A * | 8/1995 | Collinson et al. ........... 604/247 |
| 5,441,487 A | 8/1995 | Vedder |
| 5,462,255 A | 10/1995 | Rosen et al. |
| 5,466,219 A | 11/1995 | Lynn et al. |
| 5,509,433 A | 4/1996 | Paradis |
| 5,509,912 A | 4/1996 | Vaillancourt et al. |
| 5,533,983 A | 7/1996 | Haining |
| 5,535,771 A | 7/1996 | Purdy et al. |
| 5,535,785 A | 7/1996 | Werge et al. |
| 5,540,661 A | 7/1996 | Tomisaka et al. |
| 5,549,577 A | 8/1996 | Siegel et al. |
| 5,569,235 A | 10/1996 | Ross et al. |
| 5,573,516 A | 11/1996 | Tyner |
| 5,584,808 A | 12/1996 | Healy |
| 5,616,129 A | 4/1997 | Mayer |
| 5,620,434 A | 4/1997 | Brony |
| 5,624,414 A | 4/1997 | Boettger |
| 5,645,538 A | 7/1997 | Richmond |
| 5,674,206 A | 10/1997 | Allton et al. |
| 5,676,346 A | 10/1997 | Leinsing |
| 5,685,866 A | 11/1997 | Lopez |
| 5,690,612 A | 11/1997 | Lopez et al. |
| 5,694,686 A | 12/1997 | Lopez |
| 5,695,466 A | 12/1997 | Lopez et al. |
| 5,699,821 A | 12/1997 | Paradis |
| 5,700,248 A | 12/1997 | Lopez |
| 5,730,418 A | 3/1998 | Feith et al. |
| 5,738,663 A | 4/1998 | Lopez |
| 5,743,894 A | 4/1998 | Swisher |
| 5,749,861 A * | 5/1998 | Guala et al. ................ 604/249 |
| 5,776,113 A | 7/1998 | Daugherty et al. |
| 5,782,816 A | 7/1998 | Werschmidt et al. |
| 5,785,693 A | 7/1998 | Haining |
| 5,788,215 A | 8/1998 | Ryan |
| 5,806,551 A | 9/1998 | Meloul et al. |
| 5,806,831 A | 9/1998 | Paradis |
| 5,810,768 A | 9/1998 | Lopez |
| 5,810,792 A | 9/1998 | Fangrow, Jr. et al. |
| 5,810,793 A | 9/1998 | Boettger |
| 5,839,715 A | 11/1998 | Leinsing |
| 5,848,994 A | 12/1998 | Richmond |
| 5,873,862 A | 2/1999 | Lopez |
| 5,901,942 A | 5/1999 | Lopez |
| 5,921,264 A | 7/1999 | Paradis |
| 5,921,419 A | 7/1999 | Niedospial, Jr. et al. |
| 5,928,204 A | 7/1999 | Lopez |
| 5,957,898 A | 9/1999 | Jepson et al. |
| 5,967,490 A | 10/1999 | Pike |
| 5,971,950 A | 10/1999 | Lopez et al. |
| 6,019,748 A | 2/2000 | Lopez |
| 6,029,946 A | 2/2000 | Doyle |
| 6,036,171 A | 3/2000 | Weinheimer et al. |
| 6,039,302 A | 3/2000 | Cote, Sr. et al. |
| 6,045,534 A | 4/2000 | Jacobsen et al. |
| 6,063,062 A | 5/2000 | Paradis |
| 6,068,011 A | 5/2000 | Paradis |
| 6,083,194 A | 7/2000 | Lopez |
| 6,106,502 A | 8/2000 | Richmond |
| 6,113,068 A | 9/2000 | Ryan |
| 6,117,114 A | 9/2000 | Paradis |
| 6,127,320 A | 10/2000 | van Ooij et al. |
| 6,132,403 A | 10/2000 | Lopez |
| 6,132,404 A | 10/2000 | Lopez |
| 6,142,446 A | 11/2000 | Leinsing |
| 6,168,137 B1 | 1/2001 | Paradis |
| 6,170,800 B1 | 1/2001 | Meloul et al. |
| 6,171,287 B1 | 1/2001 | Lynn et al. |
| 6,189,859 B1 | 2/2001 | Rohrbough et al. |
| 6,228,069 B1 | 5/2001 | Barth et al. |
| 6,245,048 B1 * | 6/2001 | Fangrow et al. ............ 604/249 |
| 6,245,056 B1 | 6/2001 | Walker et al. |
| 6,261,282 B1 | 7/2001 | Jepson et al. |
| 6,273,869 B1 | 8/2001 | Vaillancourt |
| 6,290,206 B1 | 9/2001 | Doyle |
| 6,290,688 B1 | 9/2001 | Lopez et al. |
| 6,299,131 B1 | 10/2001 | Ryan |
| 6,299,132 B1 | 10/2001 | Weinheimer et al. |
| 6,325,782 B1 | 12/2001 | Lopez |
| 6,344,033 B1 | 2/2002 | Jepson et al. |
| 6,364,869 B1 | 4/2002 | Bonaldo |
| 6,428,520 B1 | 8/2002 | Lopez et al. |
| 6,482,188 B1 | 11/2002 | Rogers et al. |
| 6,491,668 B1 | 12/2002 | Paradis |
| 6,541,802 B2 | 4/2003 | Doyle |
| 6,572,592 B1 | 6/2003 | Lopez |
| 6,585,229 B2 | 7/2003 | Cote, Sr. et al. |
| 6,599,273 B1 | 7/2003 | Lopez |
| 6,616,627 B2 | 9/2003 | Willis et al. |
| 6,626,418 B2 | 9/2003 | Kiehne |
| 6,635,044 B2 | 10/2003 | Lopez |
| 6,641,561 B1 | 11/2003 | Hill et al. |
| 6,645,170 B2 | 11/2003 | Landau |
| 6,669,673 B2 | 12/2003 | Lopez |
| 6,669,681 B2 | 12/2003 | Jepson et al. |
| 6,682,509 B2 | 1/2004 | Lopez |
| 6,695,817 B1 | 2/2004 | Fangrow, Jr. |
| 6,706,022 B1 | 3/2004 | Leinsing et al. |
| 6,755,391 B2 | 6/2004 | Newton et al. |
| 6,758,833 B2 | 7/2004 | Lopez |
| 6,802,490 B2 | 10/2004 | Leinsing et al. |
| 6,840,501 B2 | 1/2005 | Doyle |
| 6,855,138 B2 | 2/2005 | Tsai |
| 6,869,426 B2 | 3/2005 | Ganem |
| 6,871,838 B2 | 3/2005 | Raines et al. |

* cited by examiner

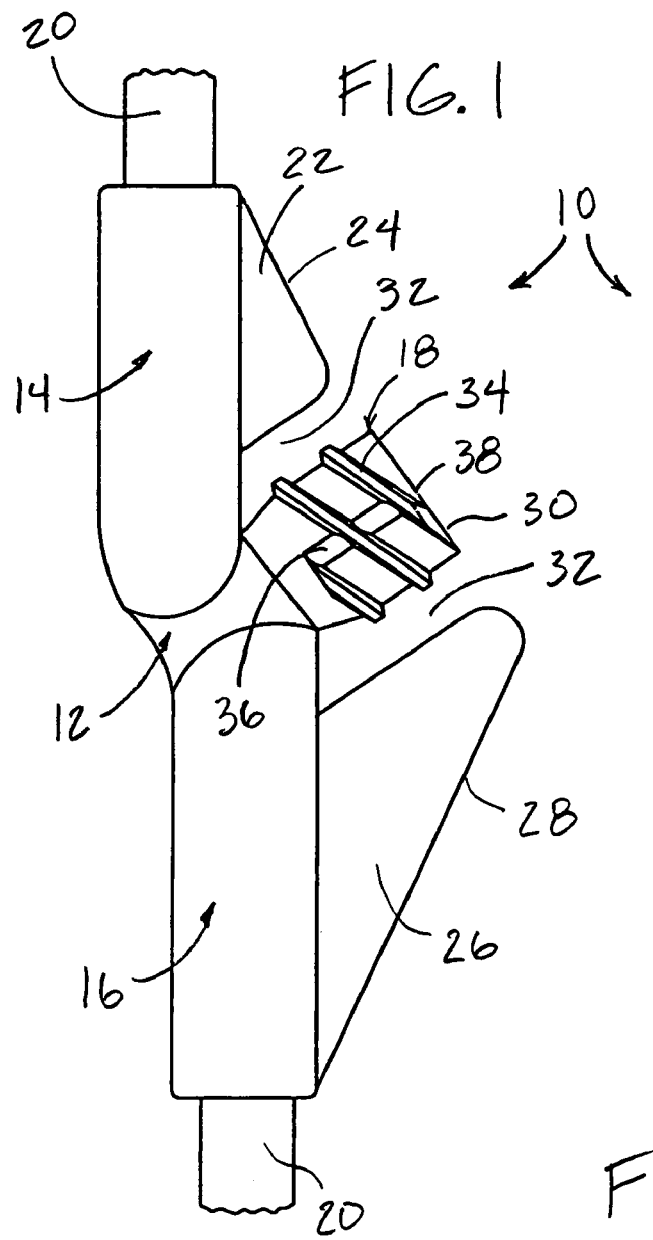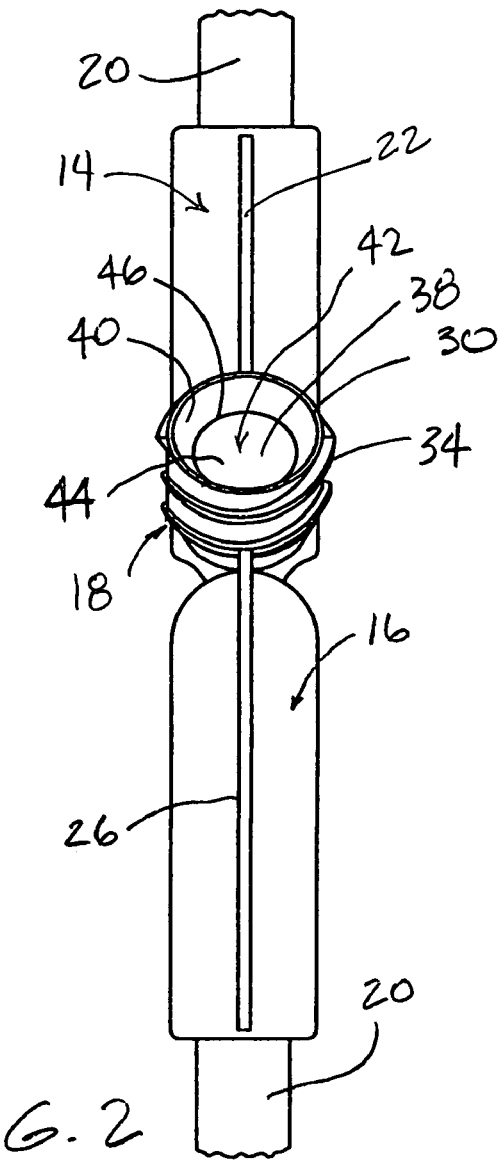

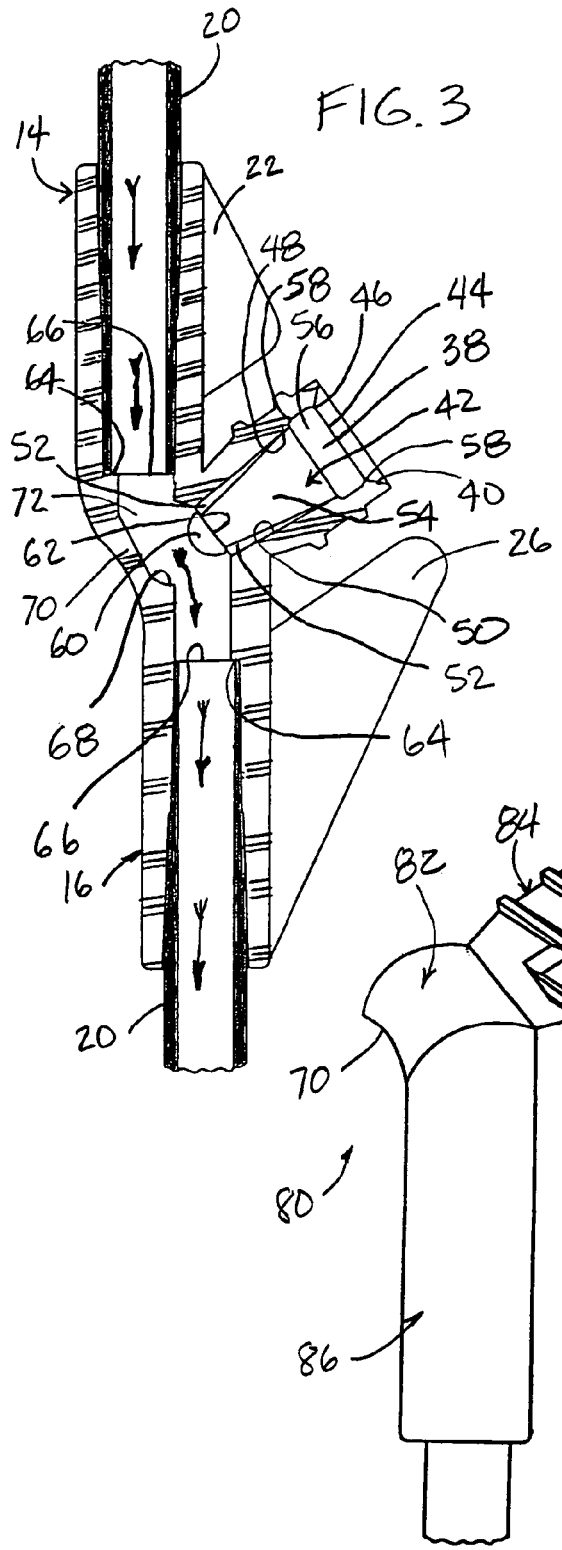
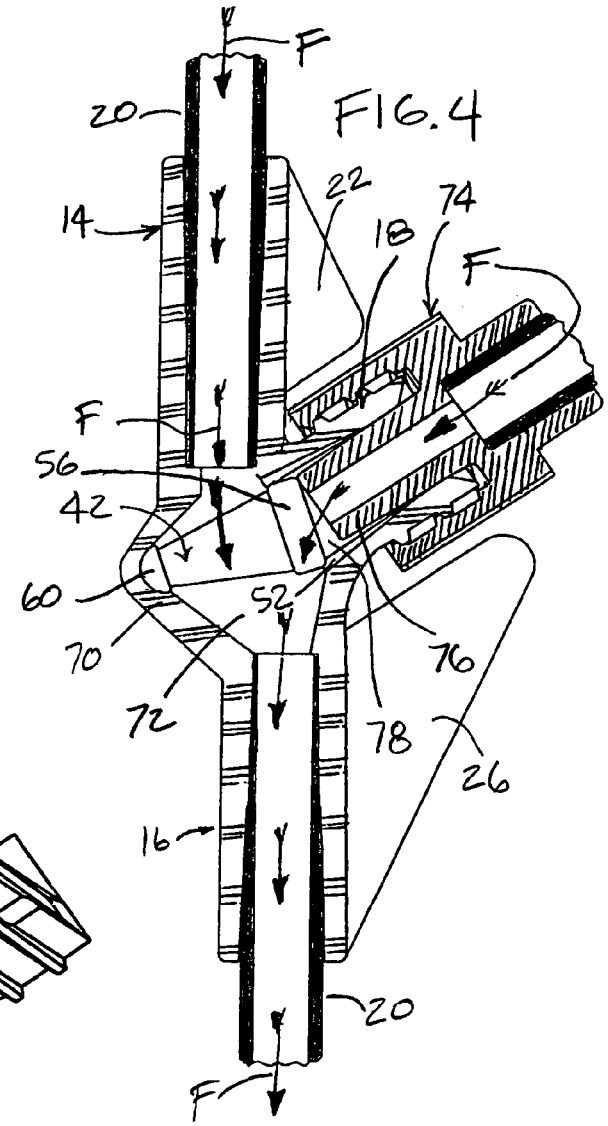
FIG. 3
FIG. 4
FIG. 5

NEEDLELESS ACCESS PORT VALVES

Needleless access port valves are generally discussed herein with particular discussions extended to needleless access port valves comprising a stretched body.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

In accordance with aspects of the present invention, there is provided a needleless injection port valve assembly comprising a valve housing comprising an inlet port, an outlet port, and a valve base; the inlet port defining an opening and an interior cavity comprising a plurality of ribs; a plug disposed in the interior cavity of the inlet port and having a first position and a second position; the first position is characterized by the plug spaced apart from the valve base and the second position is characterized by the plug abutting the valve base and urging the valve base outwardly away from the opening.

In accordance yet with other aspects of the present invention, there is provided a needleless injection port valve assembly comprising a valve housing comprising an inlet port, an outlet port, and a valve base; the inlet port defining an opening and an interior cavity comprising an upper cavity section and a lower cavity section; a plug disposed in the interior cavity of the inlet port and a plug lower section spaced apart from a deflection shoulder positioned on the valve base; and wherein the valve base is urged outwardly away from the opening when the plug moves from a first position to a second position and abuts the deflection shoulder.

In still yet another aspect of the present invention, there is provided a needleless injection port valve assembly comprising a valve housing comprising an inlet port and an outlet port; the inlet port defining an opening and an interior cavity comprising an upper cavity section and a lower cavity section; a plug disposed in the interior cavity of the inlet port; stretch means for both stretching to accommodate the plug and for pushing the plug into contact with the upper and lower cavity sections.

In still yet another aspect of the present invention, there is provided an integrally formed inlet port, outlet port, and set port.

In still yet another aspect of the present invention, there is provided a housing made from a two-part self-lubricating material.

Other aspects and variations of the valve assemblies summarized above are also contemplated and will be more fully understood when considered with respect to the following disclosure.

BRIEF DESCRIPTION OF THE DRAWINGS

These and other features and advantages of the present invention will become appreciated as the same become better understood with reference to the specification, claims and appended drawings wherein:

FIG. 1 is a semi-schematic side view of a needleless access port valve provided in accordance with aspects of the present invention;

FIG. 2 is a semi-schematic front view of the needleless access port valve of FIG. 1;

FIG. 3 is a semi-schematic cross-sectional side view of the valve of FIG. 1 in a first position;

FIG. 4 is a semi-schematic cross-sectional side view of the valve of FIG. 1 in a second position; and FIG. 5 is a semi-schematic side view of an alternative embodiment provided in accordance with aspects of the present invention.

DETAILED DESCRIPTION

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

FIG. 1 is a semi-schematic side view of an exemplary valve provided in accordance with aspects of the present invention, which is generally designated 10. In one exemplary embodiment, the valve 10 comprises a valve body 12, an inlet port 14, an outlet port 16, and a second inlet port or slip port 18 for slipping a side stream into the valve or for taking a sample therefrom. The valve is known in the industry as a Y-site valve. Preferably, the valve body 12 is integrally formed with the inlet, outlet, and slip ports 14, 16, 18. More preferably, the components are integrally formed from a thermoplastic elastomer (TPE), which has, among other things, a resilient property. In one exemplary embodiment, the TPE is a member of the copolyamide (COPA) family of thermoplastic elastomers. In a preferred embodiment, the COPA is copolyamide thermoplastic elastomer having a commercial trade name PEBAX®. However, other TPEs may also be used to make the valve body 12, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. In one exemplary embodiment, one or more colors are incorporated in the material. Preferably, the material has a translucent pantone green tone. Alternatively, an opaque material with one or more color tones or a clear finish may be incorporated.

In one exemplary embodiment, the inlet and outlet ports 14, 16 are universal tubing joints adapted to matingly engage the two tubes 20 in an interference configuration. The tubings are in turn connected to an IV system and/or a patient. In one exemplary embodiment, the inlet and outlet ports 14, 16 each defines an axis and the two axes are generally parallel and offset to one another. In an alternative embodiment, the two axes are angularly positioned to one another with an angle range of about 95 degrees to about 175 degrees being more preferred. Still alternatively, the two axes are coincident of one another.

In one exemplary embodiment, a deflection rib 22 comprising a top edge 24 is incorporated on the inlet port 14 and a bottom deflection rib 26 comprising a top edge 28 is incorporated on the outlet port 16. The two edges preferably have a contour that transitions smoothly with the top edge 30 of the second inlet port 18. The smooth contour allows the valve 10 to resist entanglement with other medical related instruments, such as IV lines, cables, and the like. By smooth, one edge should not extend outwardly disproportionately relative to one or more other edges. In a preferred embodiment, the two fins 22, 26 are generally thin and have similar gauge or thickness as the gauge or thickness of the two ports 14, 16. To further resist entanglement, gaps 32 positioned between the slip port 18 and the two deflection ribs 22, 26 are preferably smaller in dimension than the width of a typical IV line. The relative dimensions will prevent the IV line from being trapped in between the two gaps 32.

The second inlet or slip port 18 preferably includes external threads 34 and generally conforms to a standard female luer with threads. However, the slip port 18 may be a standard luer slip without incorporating external threads. One or more ribs 36 may be incorporated with the external threads 34. Preferably, if a plurality of ribs 36 are incorporated, such as two, three, and so forth, they are evenly spaced apart along the external periphery of the slip port. In a preferred embodiment, there are two evenly-spaced-apart ribs. The ribs 36 provide an interference fit with a medical implement, such as a syringe or the like, and therefore serve to further secure the medical implement to the valve 10. In one exemplary embodiment, the ribs 36 taper radially inwardly as they extend distally away from the opening 38 of the slip port 18.

FIG. 2 is a semi-schematic front view of the valve 10 of FIG. 1. The second inlet port 18 incorporates a funnel lead-in or tapered entrance 40 at the opening 38. This tapered entrance facilitates insertion of a medical implement into the opening by directing objects that come into contact therewith towards the central opening 38.

In one exemplary embodiment, a plug 42 comprising a flat upper plug surface 44 is disposed in the cavity defined by the slip port 18. As further discussed below, the plug 42 is urged against an internal lip 46 that defines the opening 38. The size of the opening 38 is smaller than the cross-sectional dimension of the plug 42 so as to delimit movement of the plug from dislodging from the slip port 18. The flat upper surface 44 allows the plug to be easily swabbable. In one exemplary embodiment, the plug is made from a rigid plastic material. Preferably, the rigid plastic material is polycarbonate, polystyrene, polypropylene, or their equivalence.

FIG. 3 is a semi-schematic cross-sectional side view of the valve 10 of FIG. 1 shown with the plug 42 in a first or closed position. The plug 42 may be inserted into the interior cavity of the slip port 18 by first applying a lubricant, such as medical grade silicone, on the interior surface of the slip port. Alternatively or in addition thereto, lubricant may be applied on the surface of the plug before inserting the same into the interior cavity of the slip port. As the slip port 18 is made from a resilient material, it will flex to accommodate the plug. Still alternatively, the plug 42 and/or the valve body 12 may be made from a self-lubricating material. In one exemplary embodiment, the self-lubricating material is a two-part self-lube liquid silicone rubber. The two-part self-lube silicone rubber is commercially available from Nusil Silicone Technology of Santa Barbara, Calif. Various aspects of the self-lube liquid silicone rubber are described in Ser. No. 10/407,001, filed Apr. 3, 2003, the contents of which are expressly incorporated herein by reference as if set forth in full. External lubricant may be eliminated when incorporating the two-part self-lubricating material.

In one exemplary embodiment, the plug is urged in the closed position (FIG. 3) by the resiliency of the slip port 18 and the geometry of the slip port relative to the plug 42. The slip port comprises an upper interior section 48 and a lower interior section 50. The upper interior section 48 comprises a luer taper for a standard luer taper contact with a corresponding male luer fitting, such as a syringe tip. The lower interior section 50 comprises a tapered wall surface having a greater taper angle than the taper of the upper interior section 48. A plurality of ribs 52 adorn the lower interior section 50. Preferably, four or more ribs are positioned in a spaced-apart relationship in the lower interior section 50. The ribs define flow channels therebetween for fluid flow flowing from a medical implement or towards the medical implement when taking a sample.

When in the closed position, the plurality of ribs 52 and the upper interior section 48 of the slip port 18 compress against the periphery of the plug 42. As the plug 42 comprises a tapered mid section 54, the compression imparts a pair of component forces against the tapered surface and pushes the plug in a proximal direction towards the opening 38. However, as previously discussed, the radially inwardly extending lip 46 blocks the plug 42 from dislodging out through the opening.

In one exemplary embodiment, the plug 42 incorporates a generally cylindrical flange section 56 comprising a generally square or straight side wall (i.e., having little or no taper) comprising an upper and a lower bevel 58. The flange section 56 helps counteract the upwardly biasing force generated by the taper upper section 48 and the ribs 52 of the slip port 18 on the plug 42. In a preferred embodiment, an anchor 60 comprising a shoulder 62 is incorporated to abut the plurality of ribs 52 to further limit the movement of the plug 42. The anchor 60 is shown comprising a dome-shape end and, in a preferred embodiment, is integrally molded to the tapered mid-section 54. However, other shaped ends may be incorporated without deviating from the spirit and scope of the present invention, such as a more pointed shaped end, an end with more straight edges, an irregular shape end, etc.

As previously discussed, the two tubes 20 are engaged to the inlet 14 and the outlet 16 ports through a standard taper contact. In one exemplary embodiment, a shoulder 64 is incorporated in the interior cavity of each port to abut with the distal end edge 66 of each tube 20. The contacts are configured to delimit the extent of insertion of the two tubes 20 into the two ports 14, 16. Although the two shoulders 64 shown comprise only a segment of the interior circumference of each port, two or more shoulder segments or a complete circular segment may be incorporated without deviating from the spirit and scope of the present invention.

In one exemplary embodiment, a deflection shoulder 68 is incorporated on the base 70 of the valve body cavity 72. As further discussed below with reference to FIG. 4, the deflection shoulder 68 is configured to deflect or tilt the plug 42 when the plug is moved distally by a medical implement and abuts the deflection shoulder 68. The tilting creates a gap (78 in FIG. 4) between the top surface 44 of the plug and the tip of the medical implement to permit fluid flow from either the medical implement or towards the medical implement, the latter when taking a sample. Alternatively or in addition thereto, protrusions may be incorporated on the top surface 44 of the plug 42. The protrusions define flow channels therebetween for fluid flow from either the medical implement or towards the medical implement without having to tilt the plug.

Referring now to FIG. 4 in addition to FIG. 3, a medical implement 74 is shown engaged to the slip port 18 and the implement tip 76 pushing the plug 42 against the base 70 into a second or used position. The base 70 is urged outwardly away from the opening 38 as the implement tip 76 pushes the plug 42 against it. The deflection shoulder 68 (FIG. 3) on the base causes the plug 42 to tilt while the base is being urged and stretched outwardly. The stretched base 70 imparts a force in the opposite direction against the plug 42, which is configured to push the plug 42 proximally towards the first position when the medical implement 74 is removed from the slip port 18. Movement of the plug 42 towards the slip port 18 is further facilitated by the plurality of ribs 52 on the slip port 18 compressing against the tapered mid section 54 of the plug 42, as previously discussed. Preferably, when the plug 42 moves distally to the second position (FIG. 4), the cylindrical flange section 56 remains in contact with the plurality of ribs 52. The ribs 52 are thus used as a guide for the plug 42 in returning to its first position.

The flow arrows F shown in FIGS. 3 and 4 depict the directions of fluid flow. The inlet port 14 and the outlet port 16 are in constant fluid communication and fluid flow is permitted therebetween irrespective of the position of the plug 42. Conversely, fluid communication between the slip port 18 and the inlet and outlet ports 14, 16 depends on the position of the plug 42.

FIG. 5 is a semi-schematic side view of an alternative valve embodiment provided in accordance with aspects of the present invention, which is generally designated 80. The valve 80 is similar to the valve 10 of FIGS. 1-4 in that it is made from the same materials and incorporates a plug that (1) stretches the base 70 of the valve body 82 when pushed by a medical implement, and (2) moves to a closed position by a force generated by the stretched base 70 and the plurality of ribs that adorn the interior cavity of the inlet port 84. The inlet port 84 and the outlet port 86 are only in fluid communication depending on the position of the plug (not shown). In a plug first position, fluid communication between the two ports 84, 86 is terminated. In a plug second position, fluid communication between the two ports 84, 86 is opened.

Although limited embodiments of the needleless access valve assemblies and their components have been specifically described and illustrated herein, many modifications and variations will be apparent to those skilled in the art. For example, the various valves may incorporate luer-slips rather than luer threads, both the plug and the pliable valve body may be made from a two-part self-lubricating silicone rather than a TPE material, the material selected could be opaque or semi-opaque, the various dimensions can vary, etc. Furthermore, it is understood and contemplated that features specifically discussed for one valve embodiment may be adopted for inclusion with another valve embodiment, provided the functions are compatible. For example, protrusions discussed for the upper surface of the plug with reference to the valve of FIGS. 3 and 4 may be incorporated in the valve of FIG. 5. Moreover, while certain nomenclatures are used to describe various components of the preferred valves, other names may be used without deviating from the spirit and scope of the present invention. Accordingly, it is to be understood that the valve assemblies and their components constructed according to principles of this invention may be embodied other than as specifically described herein. The invention is also defined in the following claims.

What is claimed is:

1. A needleless injection port valve assembly comprising a valve housing comprising an inlet port, an outlet port, and a valve base; the inlet port defining an opening and an interior cavity comprising a plurality of ribs; a plug disposed in the interior cavity of the inlet port and having a first position and a second position; the first position is characterized by the plug spaced apart from the valve base and the second position is a valve open position characterized by the plug abutting the valve base and deflecting the valve base outwardly away from the opening.

2. The needleless injection port valve assembly of claim 1, further comprising a second inlet port, which is in constant fluid communication with the outlet port.

3. The needleless injection port valve assembly of claim 1, wherein the plug comprises a tapered body and a lower section comprising a first dimension.

4. The needleless injection port valve assembly of claim 3, wherein the plug further comprises an anchor comprising a second dimension larger than the first dimension of the lower section.

5. The needleless injection port valve assembly of claim 1, wherein the plurality of ribs comprise four spaced apart ribs.

6. The needleless injection port valve assembly of claim 1, further comprising a deflection rib positioned on an exterior surface of the outlet port.

7. The needleless injection port valve assembly of claim 1, wherein the inlet port comprises a female threaded luer.

8. The needleless injection port valve assembly of claim 1, further comprising a shoulder in an interior cavity of the outlet port.

9. The needleless injection port valve assembly of claim 1, wherein the valve housing is made from a thermoplastic elastomer (TPE) material.

10. A needleless injection port valve assembly comprising a valve housing comprising an inlet port, an outlet port, and a valve base; the inlet port defining an opening and an interior cavity comprising an upper cavity section and a lower cavity section; a plug disposed in the interior cavity of the inlet port and a plug lower section spaced apart from a deflection shoulder positioned on the valve base; and wherein the valve base is deflected outwardly away from the opening when the plug moves from a first position to a second position and abuts the deflection shoulder.

11. The needleless injection port valve assembly of claim 10, further comprising a second inlet port, which is in constant fluid communication with the outlet port.

12. The needleless injection port valve assembly of claim 10, further comprising a plurality of ribs disposed in the interior cavity of the inlet port.

13. The needleless injection port valve assembly of claim 10, wherein the plug lower section is in contact with the lower cavity section of the inlet port.

14. The needleless injection port valve assembly of claim 10, further comprising a deflection rib positioned on an exterior surface of the outlet port.

15. The needleless injection port valve assembly of claim 10, wherein the valve housing is made from a TPE material.

16. A needleless injection port valve assembly comprising a valve housing comprising an inlet port and an outlet port; the inlet port defining an opening and an interior cavity comprising an upper cavity section and a lower cavity section; a plug disposed in the interior cavity of the inlet port; stretch means for stretching to accommodate the plug when a downward force is acting on the plug and for automatically pushing the plug into contact with the upper and lower cavity sections when the downward force is removed wherein the stretch means comprises an exterior wall of the valve housing.

17. The needleless injection port valve assembly of claim 16, further comprising a second inlet port, which is in constant fluid communication with the outlet port.

18. The needleless injection port valve assembly of claim 16, wherein the stretch means is made from a TPE material.

19. The needleless injection port valve assembly of claim 16, further comprising a plurality of ribs disposed in the interior cavity of the inlet port.

* * * * *